(12) United States Patent
Wahl et al.

(10) Patent No.: US 6,228,086 B1
(45) Date of Patent: May 8, 2001

(54) MODULAR INTRAMEDULLARY NAIL (75) Inventors: Thomas Wahl, Lengnau (CH); Volker Bühren, Murnau (DE)

(73) Assignee: Stryker Trauma-Selzach AG (CH)

( * ) Notice: Subject to any disclaimer, the term of this patent is extended or adjusted under 35 U.S.C. 154(b) by 0 days.

(21) Appl. No.: 09/180,991

(22) PCT Filed: Mar. 19, 1998

(86) PCT No.: PCT/IB98/00406

§ 371 Date: Jul. 21, 1999

§ 102(e) Date: Jul. 21, 1999

(87) PCT Pub. No.: WO98/41161

PCT Pub. Date: Sep. 24, 1998

(30) Foreign Application Priority Data

Mar. 19, 1997 (EP) .................................. 97810164

(51) Int. Cl.[7] .................................. A61B 17/72
(52) U.S. Cl. .................................. 606/67; 606/62
(58) Field of Search .................................. 606/62, 67, 68

(56) References Cited

U.S. PATENT DOCUMENTS

| | | | |
|---|---|---|---|
| 5,041,115 | * 8/1991 | Frigg et al. | 606/67 |
| 5,201,735 | * 4/1993 | Chapman et al. | 606/67 |
| 5,549,610 | * 8/1996 | Russell | 606/62 |
| 5,573,536 | * 11/1996 | Grosse et al. | 606/67 |
| 5,653,709 | * 8/1997 | Frigg | 606/62 |
| 5,766,174 | * 6/1998 | Perry | 606/67 |
| 5,855,579 | * 1/1999 | James et al. | 606/67 |

FOREIGN PATENT DOCUMENTS

| | | |
|---|---|---|
| 85 33 134 | 5/1986 | (DE) . |
| 94 01 916 | 5/1994 | (DE) . |
| WO 94/13219 | 6/1994 | (WO) . |

* cited by examiner

Primary Examiner—Paul J. Hirsch
(74) Attorney, Agent, or Firm—Lerner, David, Littenberg, Krumholz & Mentlik, LLP

(57) ABSTRACT

An intramedullary nail apparatus comprises a nail having a proximal portion, a middle portion and a distal portion. The proximal portion has a longitudinal slot adapted to receive at least one fixing element and the distal portion has at least one transverse bore. The proximal portion has a longitudinal axial bore. The apparatus further includes a set of inserts, each of which is adapted to be inserted in the longitudinal bore. Each insert has at least one guiding bore, the orientation and position of which is different for each of the inserts. A method of treating fractures utilizing the intramedullary nail apparatus is also disclosed.

10 Claims, 7 Drawing Sheets

MODULAR INTRAMEDULLARY NAIL

BACKGROUND OF THE INVENTION

The present invention refers to a modular intramedullary nail, more particularly to a modular femoral intramedullary nail comprising a nail which is composed of a proximal portion, a middle portion and a distal portion, said proximal portion having a longitudinal slot and said distal portion having at least one transversal bore.

So-called unreamed locking intramedullary nails have been used for the treatment of fractures of tubular bones for some time now. Lately, the indications of such intramedullary nails have been extended to include proximal fractures of the femur shaft, these fractures existing in a great diversity while their treatment is extremely complex. As a consequence, a great number of intramedullary nails have been developed which take into account the different types of fractures. These nails only distinguish themselves by the manner in which the proximal fixing screws are positioned according to the type of fracture. This leads to an expensive storage of a large number of nails and instruments. Furthermore, it is increasingly difficult for the surgeon and the nurses to master a great number of different implant systems in such a manner that an optimum treatment of fractures is ensured.

WO-94/13219 describes an unreamed intramedullary nail of modular structure which allows a considerable reduction of the number of required intramedullary nails by its diversity in use. The intramedullary nail is provided with a cylindrical sleeve which is adapted to be slid over its proximal end in a telescopic manner and whose design allows different modes of attachment in order to adapt the intramedullary nail to the required application. However, such a telescopic attachment is not optimal with respect to biomechanical aspects, which must be considered as essential on account of the great loads at the proximal femur, and furthermore, the proximal portion of the nail is additionally thickened by the attached sleeve, thus resulting in negative effects with respect to the vascularization of the neck area of the femur head. Finally, the telescopic attachment compulsorily lengthens the nail, resulting in a modification of its original length.

DE 85 33 134 U describes a device for treating a bone fracture, which comprises a proximal hollow portion accepting a threaded bolt for fixing a screw in a transversal slot. This device is designed for a particular type of fracture and does not permit the reduction of required intramedullary nails.

SUMMARY OF THE INVENTION

On the background of this prior art, it is the object of the present invention to provide a modular intramedullary nail and a relating method where the above-mentioned drawbacks are eliminated and which has an increased biomechanical stability and ensures a better vascularization. This object is attained by an intramedullary nail wherein the proximal portion comprises a longitudinal bore extending over the longitudinal extension of said slot in the distal direction and an insert which is intended to be inserted in said longitudinal bore, said insert comprising at least one guiding bore which is intended to receive fixing elements.

BRIEF DESCRIPTION OF THE DRAWINGS

The invention is explained in more detail hereinafter with reference to drawings of several embodiments of the invention.

DETAILED DESCRIPTION OF THE PREFERRED EMBODIMENT

Nail 1 is essentially in the form of a cylindrical bar and may be divided into a proximal portion 2, a middle portion 3, and a distal portion 4. The illustrated nail for the femur is adapted to the anatomy of the femur and therefore curved according to a so-called antecurvation. The distal portion as well as the middle portion are so dimensioned that the nail can be introduced into the intramedullary channel without drilling by means of a guiding wire. Within other embodiments cannulated nails can be used.

Proximal portion 2 is cylindrical and is provided with- a longitudinal bore 5 comprising a partial internal thread 6 whose core diameter is slightly greater than the diameter of longitudinal bore 5. Bore 5 serves to receive an insert 7 whose function will be explained later on. The proximal end 11 of the proximal portion comprises two guide grooves 12 which serve for the rotationally fixed guidance of the non-represented driving bow on which, according to the indication, the corresponding aiming appliance is fastened in an angularly stable manner. Therefore, at this end of longitudinal bore 5, the internal thread is omitted in order to prevent gripping between the grooves and the fastening screw of the aiming appliance.

Proximal portion 2 is further provided with a throughgoing slot 8 which extends in parallel to the longitudinal axis. A guiding pin 9, which serves for a rotationally fixed positioning of insert 7, is disposed inside longitudinal bore 5 and transversally thereto. Underneath longitudinal bore 5, which extends beyond the longitudinal extension of slot 8 in the distal direction, the proximal portion is provided with a transversal bore at its distal end.

Middle portion 3 and distal portion 4 of the nail have a smaller diameter than the cylindrical proximal portion 2.

Figure 2:
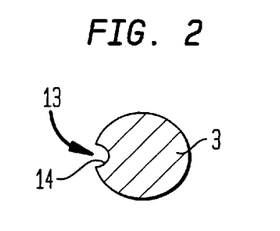
FIG. 2 shows a cross-section according to II—II in FIG. 1.
Figure 3:
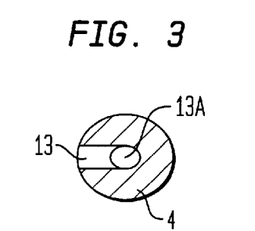
FIG. 3 shows a cross-section according to III—III in FIG. 1.
Figure 4:
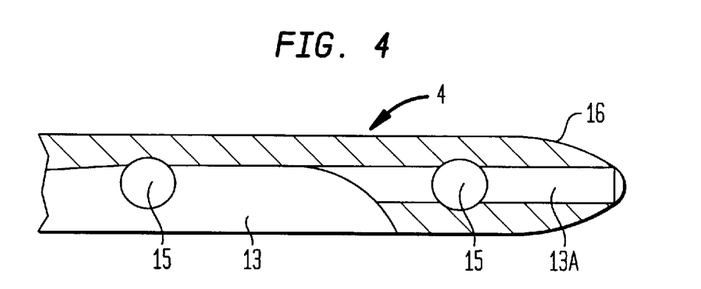
FIG. 4 shows an enlarged detail of the distal nail end according to FIG. 1.

Cross-sections II—II and III—III show that the middle portion is provided at its proximal end with a wire groove 13 intended to receive a guiding wire, the wire groove extending from the distal portion to the proximal side and being inclined with respect to the longitudinal axis of the nail. As a consequence, wire groove 13 exits from the nail below proximal portion 4, as appears in FIGS. 3 and 4, while assuming the shape of a wire channel 13A.

Bottom 14 of the groove (see FIG. 2) is rounded in order to provide an optimum guidance of the guiding wire and to prevent possible notch tensions in the bottom of the wire groove. This kind of guidance allows a safe and controlled introduction of the nail by means of the guiding wire while preventing, -in contrast to a cannulation, the formation of a non-vascularized clearance.

As already mentioned above, wire groove 13 and wire channel 13A to are provided on distal portion 4, which means that the design of the guiding means for the guiding wire allows a nail which need not be entirely cannulated while the cross-section of the nail, which is smaller due to the wire groove, reduces the risk of a fat embolism in the course of the introduction of the nail.

However, in order to carry out the invention, it is not absolutely necessary to provide the middle and the distal portions with a wire groove and a wire channel. A central cannulation of the intramedullary nail is also possible.

The lower section of the distal portion is provided with transversal bores 15. Point 16 of the nail is parabolical in order to be passed over the line of fracture without a great resistance. Transversal bores 15, of which preferably at least two are provided, serve to receive the distal fixing screws 17. As the case may be, a non-represented longitudinal slot may additionally be provided on distal portion 4.

Figure 5:
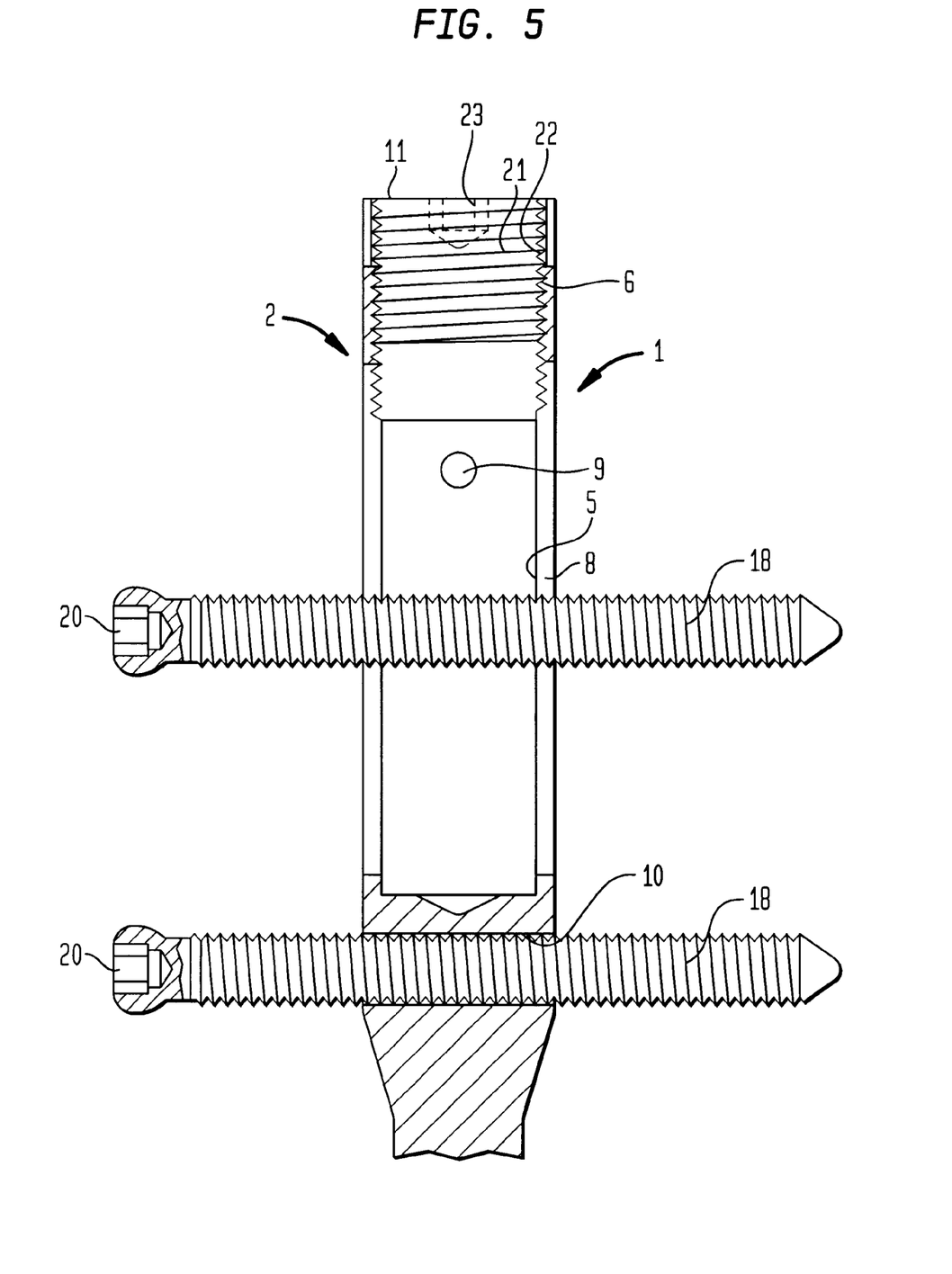
FIG. 5 shows the intramedullary nail for treating fractures in the central area of the shaft according to a second embodiment of the invention.
Figure 6:
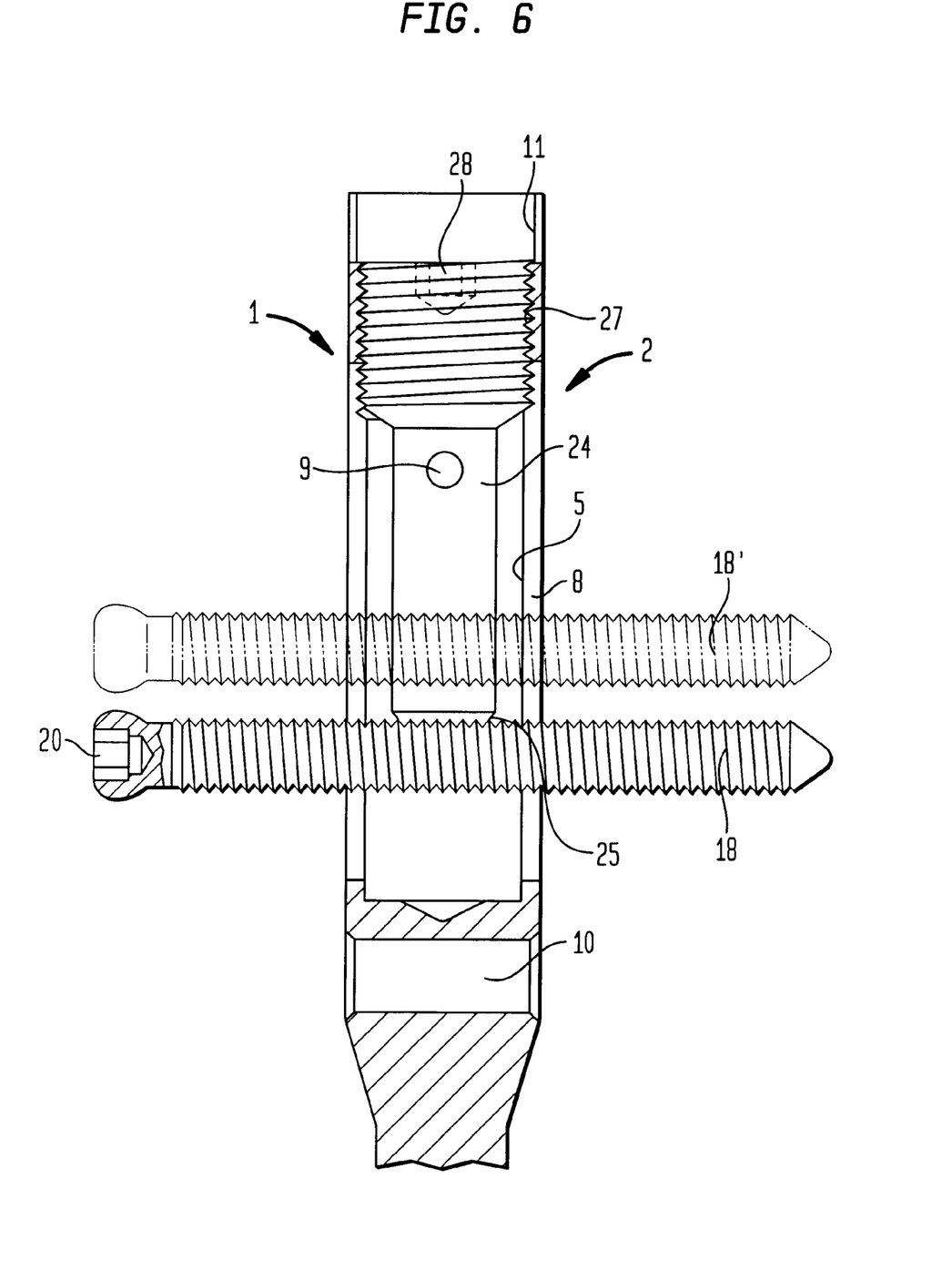
FIG. 6 shows the intramedullary nail for treating fractures in the central area of the shaft with means of a compression screw according to a third embodiment of the invention.

For the treatment of fractures in the central area of the shaft, the intramedullary nail according to FIGS. 5 and 6 may be used where the axial and torsional forces are absorbed by fixing screw 18 in transversal hole 10 as well as by a second fixing screw 18 in slot 8 which receives torsional forces exclusively. Instead of fixing screws 18, fixing bolts 19 (see FIGS. 7 and 8) may be used which are provided with hexagon sockets 20. These fixing screws 18 and fixing bolts 19 constitute the fixing elements 18 and 19.

Longitudinal bore 5 is protected against an accretion of tissue into the threaded portion, which would impair the attachment of the explantation instrument, by means of a cap screw 21. Cap screw 21 is externally threaded and comprises a hexagonal socket 23 which allows to fasten the screw.

Figure 10:
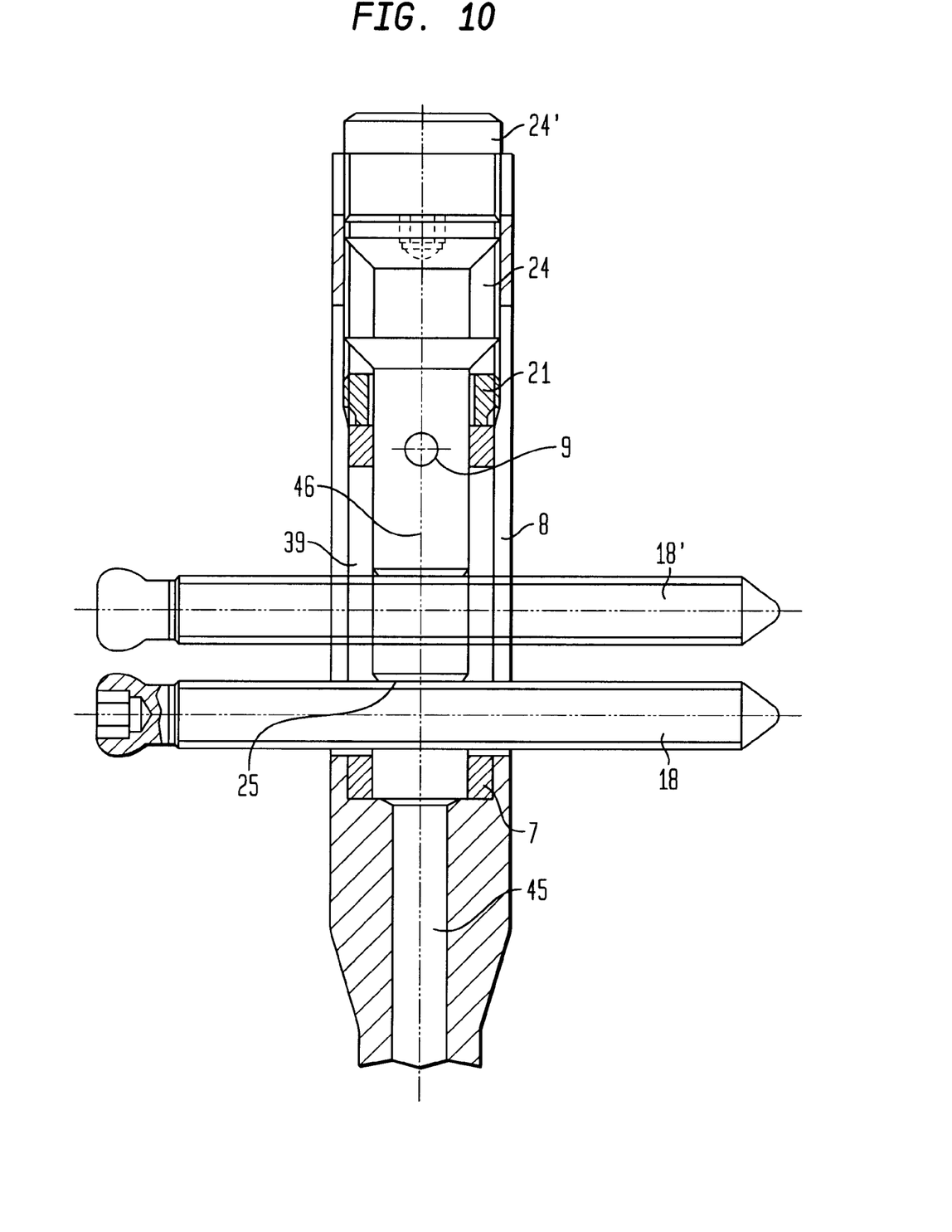
FIG. 10 shows the intramedullary nail for treating fractures in the central area of the shaft with means of a compression screw according to a seventh embodiment of the invention.

In the treatment of a fracture of the central shaft area, an active compression fixation can be effected by means of a compression screw 24 (see FIGS. 6 or 10). For this purpose, fixing screw 18 is introduced into longitudinal slot 8 transversally to the longitudinal axis of the nail by means of the proximal aiming appliance (not shown). Subsequently, compression screw 24 is entered in proximal thread 6 of the proximal portion until it contacts fixing screw 18 by its distal end 25. As the compression screw is now further entered, the proximal fragment of the bone is displaced relative to the nail until the fracture is closed and an interfragmentary compression is obtained. Compression screw 24 further comprises a shaft portion 26 which is followed by an externally threaded portion 27 of greater diameter, as well as a hexagon socket 28.

As an essential extension of the field of applications of the intramedullary nail according to the invention, more particularly for an antegrade or a retrograde fixation, an insert 7 is provided which may either be hollow or solid in design.

Figure 1:
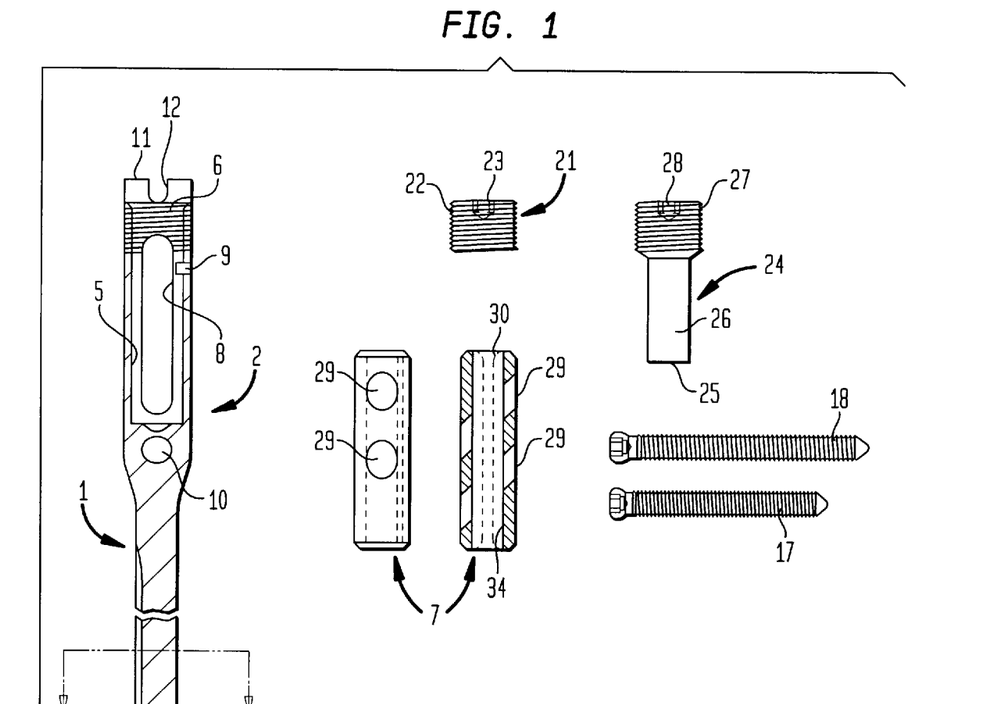
FIG. 1 shows an assembly of the different elements of the intramedullary nail in a partly sectioned view according to a first embodiment of the invention.

Insert 7 according to the embodiment shown in FIG. 1 and 5 comprises a through-going longitudinal bore 34 and two guiding bores 29 which are inclined with respect to the longitudinal axis, more than two guiding bores being possible, but at least one such bore being provided. In this case, the external diameter of cap screw 21 approximately corresponds to the external diameter of insert 7, thus allowing its fastening. A subsequent displacement of the insert in the longitudinal bore is thus prevented, i.e. a precisely defined positioning of the insert with respect to the longitudinal axis is ensured. Furthermore, the clamping action excludes any microscopic movements between the inner wall of the bore and the insert which might result in an undesirable abrasion. Finally, the insert increases the biomechanical stability of the nail by a bracing effect.

Guiding bores 29, which are inclined with respect to the longitudinal axis, may have different diameters and serve to receive fixing screws 18 or fixing bolts 19. The insert further comprises a guiding groove 30 in which guiding pin 9 engages and thus ensures a correct introduction of the insert in such a manner that guiding bores 29 for the fixing screws are aligned with respect to slot 8 of the nail. In order to facilitate the insertion, the guiding groove is enlarged in the manner of a funnel at both its ends. For a retrograde fixation of the fracture, guiding bores 29 a preferably aligned at an angle of 120° to 150° with respect to the longitudinal axis, while they are preferably aligned at an angle of 125° to 150° with respect to the longitudinal axis in the case of an antegrade fixation.

Guiding pin 9 engaging guiding groove 30 can be replaced by other elements for preventing a misalignment of insert 7. These elements can especially be integrated into the implantation instrument.

Figure 7:
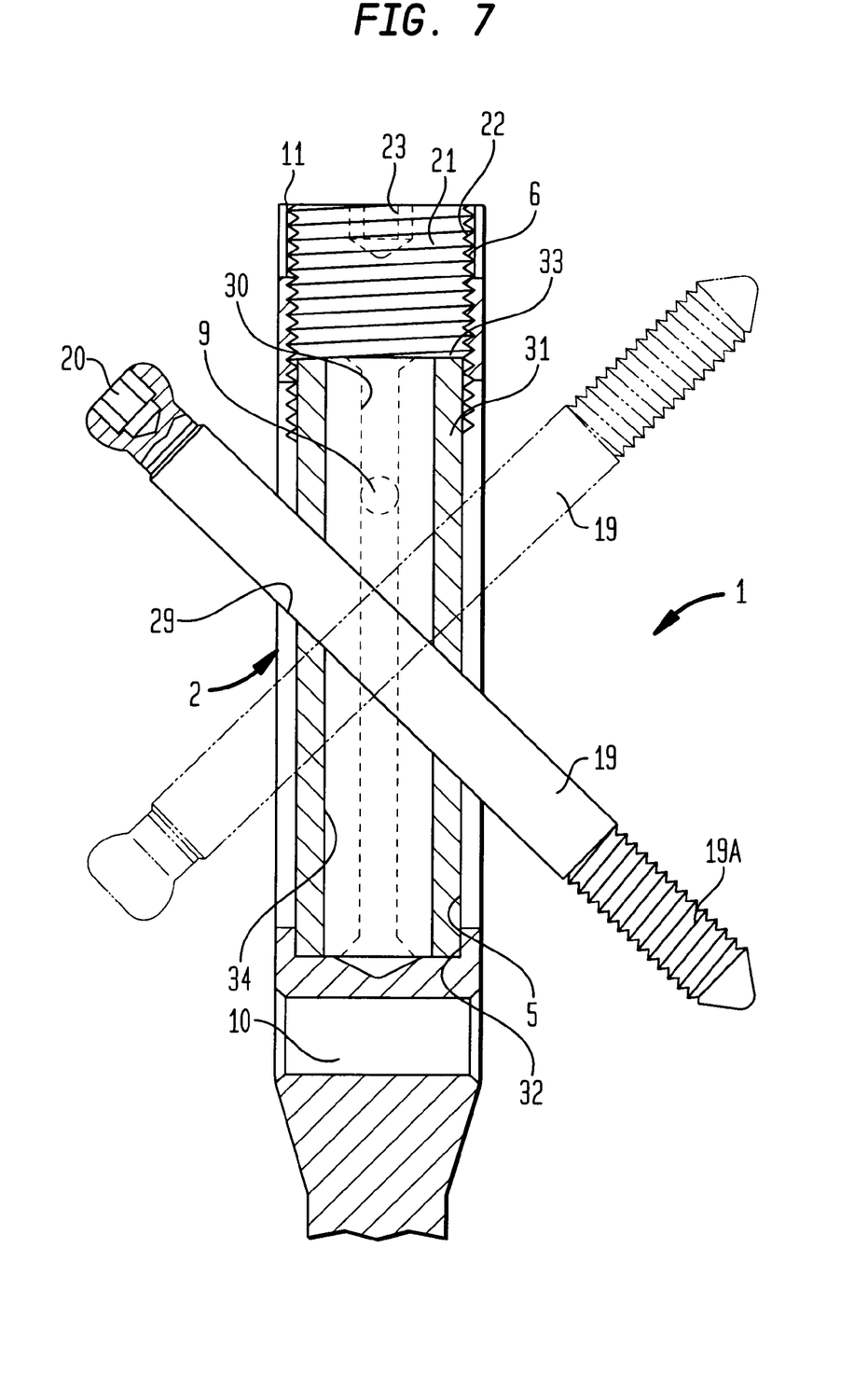
FIG. 7 shows the intramedullary nail for treating proximal femur fractures with means of a retrograde respectively an antegrade fixation according to a fourth embodiment of the invention.

FIG. 7 shows the retrograde respectively antegrade fixation of a fracture by means of an insert 31 for a intramedullary nail according to a fourth embodiment comprising a single guiding bore 29 but which is otherwise identical to insert 7. In this FIG. 7 as well as in FIG. 8, it is visible how guiding pin 9 engages in guiding groove 30 of the insert and thus precisely aligns the insert with respect to longitudinal slot 8. It further appears that, an insertion of the sleeve with one of its ends 32 facing in the distal direction or with the other end 33 facing in the distal direction allows either a retrograde or an antegrade fixation. In this case, as in the case according to FIG. 8, the cap screw 21 serves to fasten the insert by a clamping action and furthermore as a protection against an accretion of tissue into the threaded portion.

Figure 8:
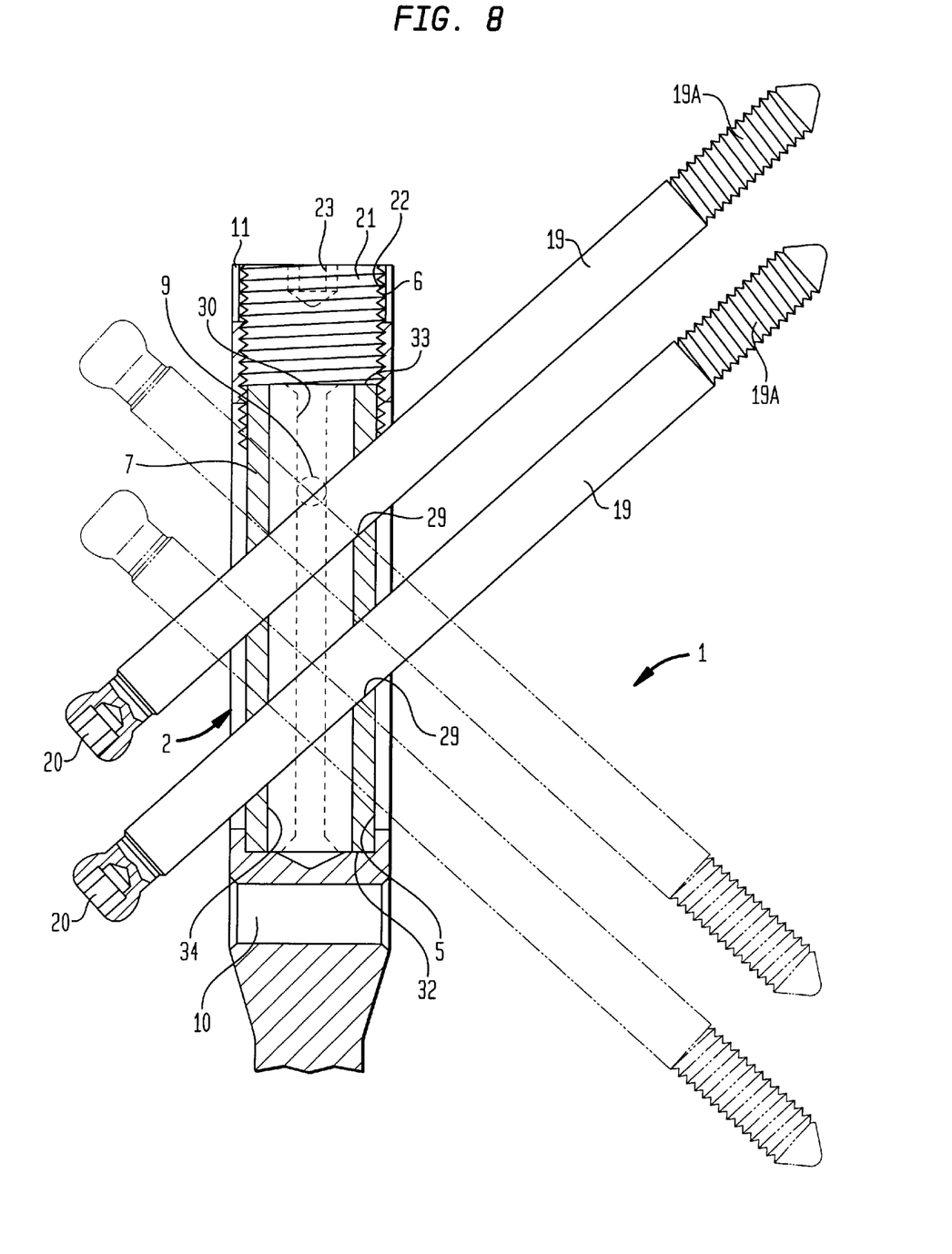
FIG. 8 shows the intramedullary nail for treating proximal femur fractures with means of a retrograde respectively an antegrade fixation according to a fifth embodiment of the invention.

FIG. 8 shows the use of insert 7 for a intramedullary nail according to a fifth embodiment with two guiding bores 29 in the case of a retrograde respectively an antegrade fixation of the fracture. The considerations with regard to insert 31 according to FIG. 7 apply in an analogous manner.

Figure 9:
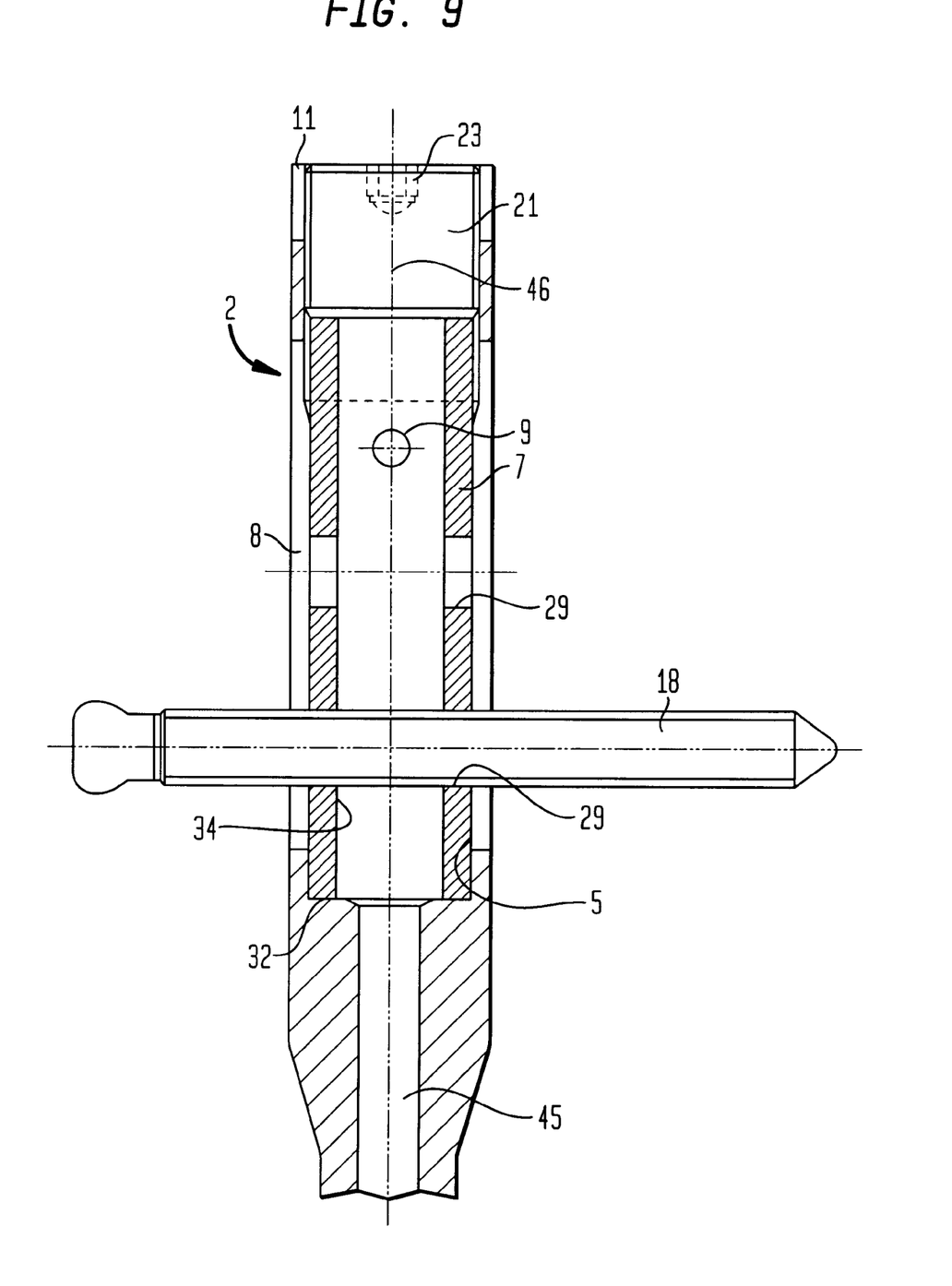
FIG. 9 shows the intramedullary nail for treating fractures in the central area of the shaft according to a sixth embodiment of the invention.

FIG. 9 shows a intramedullary nail for treating fractures in the central area of the shaft according to a sixth embodiment of the invention. The nail is cannulated and comprises a throughgoing slot 45 which extends in parallel to the longitudinal axis. Underneath longitudinal bore 5 which extends beyond the longitudinal extension of slot 8 in the distal direction, the proximal portion does not contain a transversal bore at its distal end. Insert 7 comprises at least one guiding bore 29. In the embodiment shown insert 7 comprises two guiding bores 29 which are oriented transversal to the longitudinal axis 46 of insert 7 respectively proximal portion 2. Fixing screws 18 are received within said guiding bores 29 whereby another screw is provided in the distal portion 4 to stabilise a fracture of the central area of the shaft.

FIG. 10 shows a intramedullary nail for treating fractures in the central area of the shaft according to a seventh embodiment of the invention using a compression screw 24 to effect an active compression fixation. First of all insert 7 comprising a longitudinal guiding slot 39 is introduced and fixed by means of the cap screw 21. Then, the fixing screw 18 is pushed through the longitudinal guiding slots 39 and 8 in a direction transversal to the longitudinal axis 46 of the nail. The initial position of the fixing screw is marked with numeral 18'. Finally, the compression screw 24 is inserted into the internal thread 6 of the proximal portion until contacting the fixing screw 18' in the position 24'. The shaft of the compression screw 24 transverses the hollow cap screw 21. As the compression screw 24 is now further entered, the proximal fragment of the bone is displaced relative to the nail until the fracture is closed and an interfragmentary compression is obtained. The distal end 25 of the compression screw 24 touches the fixing screw 18 in the position shown in unbroken lines.

The intramedullary nail shown and described is to be used for femur fractures. It is clear that the nail can also be provided for treatment of other fractures, e.g. fractures of the tibia or the humerus. The basic advantage of the modular system of this intramedullary nail using inserts which do not enlarge the space used for the nail is maintained.

It follows from the preceding description that a nail 1 as well as a limited number of inserts allow to treat all kinds of femur, tibia and humerus shaft fractures as well as the most different proximal femur, tibia or humerus fractures. Besides, the shape of the inserts and thus also of the longitudinal bore 5 receiving the insert is independent from the diameter or the length of the nail. Furthermore, there is no need for a left-hand and a right-hand form of the nail, which is an essential advantage with respect to the use and the storage of this implant. The corresponding left-hand or right-hand embodiment of the nail is determined by a mere 180° turn when introducing the insert. It further follows from the description that other embodiments of the intramedullary nail such as reconstruction nails can be used according to the inventive idea.

What is claimed is:

1. An intramedullary nail comprising a nail which is composed of a proximal portion, a middle portion and a distal portion, said proximal portion having a longitudinal slot extending throuqh the proximal portion in a direction transverse to the longitudinal axis of the proximal portion and being adapted to receive at least one fixing element extending therethrough and said distal portion having at least one transversal bore, the proximal portion having a longitudinal axial bore extending over the longitudinal extension of said slot and a set of inserts each of which is adapted to be inserted in said longitudinal bore, each of said inserts comprising at least one guiding bore to receive said fixing element, the orientation and the position of said guiding bore being different for each insert of said set of inserts.

2. The intramedullary nail of claim 1, wherein the alignment of the guiding bores of said inserts are inclined with respect to the longitudinal axis of the proximal portion and wherein said inserts are adapted to be inserted and locked in said longitudinal bore with one end facing the distal direction for retrograde fixation and with the other end facing the distal direction for antegrade fixation.

3. The intramedullary nail of claim 1, wherein the alignment of the guiding bores of each of said inserts is transverse with respect to the longitudinal axis of the proximal portion.

4. The intramedullary nail of claim 1, further including a guiding pin which engages in the longitudinal bore of said proximal portion, and wherein at least one of said inserts is provided with a corresponding guiding groove for its correctly positioned insertion.

5. The intramedullary nail of claim 1, wherein the longitudinal bore of said proximal portion is internally threaded and provided with a cap screw.

6. The intramedullary nail of claim 1, wherein at least one of said inserts and said nail is hollow.

7. The intramedullary nail of claim 1, wherein said fixing element comprises a fixing element selected from the group consisting of fixing screws, fixing bolts, and blades.

8. An intramedullary nail comprising a nail (1) which is composed of a proximal portion, a middle portion and a distal portion, said proximal portion having a longitudinal slot and said distal portion having at least one transversal bore, said middle portion and said distal portion of the nail being provided with a wire groove which ends in a wire channel (13A) at the distal end.

9. The intramedullary nail of claim 8, wherein the bottom of said wire groove is rounded.

10. A method of treating fractures comprising the steps of:

(a) placing a nail in the intramedullary space of a bone, the nail having a longitudinal axis and a proximal portion, a middle portion and a distal portion, the proximal portion having a longitudinal slot and the distal portion having at least one transverse bore, whereby the proximal portion includes a longitudinal bore extending over the longitudinal extension of the slot in the distal direction;

(b) introducing at least one distal fixing screw in the at least one transverse bore;

(c) selecting an insert from a set of inserts, each of said inserts having at least one guiding bore, the orientation and position of the guiding bore being different for each insert of the set of inserts;

(d) introducing the selected insert in said longitudinal bore, the insert having at least one guiding bore; and (e) driving one fixing element in the at least one guiding bore of the insert and through the longitudinal slot of the nail.

\* \* \* \* \*